United States Patent [19]

Liu et al.

[11] Patent Number: 5,017,563

[45] Date of Patent: May 21, 1991

[54] CASTANOSPERMINE ESTERS AND GLYCOSIDES

[75] Inventors: Paul S. Liu; Barry L. Rhinehart, both of Cincinnati, Ohio; John K. Daniel, Indianapolis, Ind.

[73] Assignee: Merrell Dow Pharmaceuticals Inc., Cincinnati, Ohio

[21] Appl. No.: 519,350

[22] Filed: May 1, 1990

Related U.S. Application Data

[63] Continuation of Ser. No. 274,584, Nov. 22, 1988, abandoned, which is a continuation-in-part of Ser. No. 69,351, Jul. 2, 1987, abandoned.

[30] Foreign Application Priority Data

Jun. 23, 1988 [CA] Canada .................................. 570177

[51] Int. Cl.$^5$ .................. C07D 471/04; A61K 31/445
[52] U.S. Cl. ........................................ 514/27; 514/66; 514/299; 514/866; 536/17.3; 546/183
[58] Field of Search ..................... 536/17.3; 546/183; 514/27, 66, 299

[56] References Cited

FOREIGN PATENT DOCUMENTS 227566 10/1986 Japan .

OTHER PUBLICATIONS

L. D. Hohenschutz et al., *Phytochemistry,* 20(4), 811–814 (1981).
D. L. Dreyer et al., *Journal of Chemical Ecology,* 11(8), 1045–51 (1985).
P. S. Sunkara et al., Society for Complex Carbohydrates, 17th Annual Mtg., San Antonio, Tex., *Glycosidase Inhibitors as Antivirals Against Human Immunodificiency Virus* (HIV) (Abstract Provided).
Sue Armstrong, *Tree Compounds May Strip the Virus of its Powers, New Scientist,* 120 (1640), 23 (1988).
J. Chattopadhyaya, JCS Chem. Comm., 1979, p. 987.
Sunkara, Abstract 9 and Slides from 17th Annual Meeting of Society for Complex Carbohydrates, 11-3-88.
Tommila, Chem. Abs. 35, 6172 (1944).
Bender, J. Amer. Chem. Soc., 87, 4545 (1965).
Greene, "Protective Groups in Organic Chemistry", pp. 62–63.
Hohenschutz, Chem. Abs. 95, 202446 (1981).
Bernotas, Chem. Abs. 100, 192129b (1984).
Setoi, Chem. Abs. 105, 24481v (1985).
Campbell, Chem. Abs. 107, 215128m (1987).
Saul et al., Chem. Abs. 102, 126770u (1985).
Saul et al., Chem. Abs. 98, 139631y (1983).
Palmarczyk, Chem. Abs. 103, 20519z (1985).
Chambers, Chem. Abs. 105, 129836t (1986).

*Primary Examiner*—Mark L. Berch
*Attorney, Agent, or Firm*—John J. Kolano

[57] ABSTRACT

Castanospermine mono- and di-esters and glycosides active as inhibitors of carbohydrate digestive enzymes and useful in treating diabetes are described herein. The compounds are prepared by the reaction of castanospermine with an appropriate acid halide or anhydride or with an appropriate glycosyl halide or glycosyl acetimidate under conditions which would favor the isolation of the mono- and di-esterified and glycosylated products. Various blocking groups, which can be selectively removed under mild conditions, can also be used to favor the formation of certain isomers.

22 Claims, No Drawings

CASTANOSPERMINE ESTERS AND GLYCOSIDES

This is a continuation of application Ser. No. 274,584, filed Nov. 22, 1988, which is a continuation-in-part of application Ser. No. 69,351, filed July 2, 1987, (both now abandoned).

BACKGROUND OF THE INVENTION

Castanospermine is an alkaloid which has been isolated from the seeds of *Castanospermum australe* and it has the following formula:

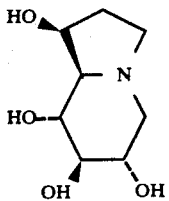

Systematically, this compound can be named in several ways as follows: [1S-(1α, 6β, 7α, 8β, 8αβ)]-octahydro-1,6,7,8-indolizinetetrol or (1S,6S,7R,8R,8αR)-1,6,7,8-tetrahydroxyindolizidine or 1,2,4,8-tetradeoxy-1,4,8-nitrilo-L-glycero-D-galacto-octitol. The term "castanospermine" or the first systematic name will be used in the discussion below.

The isolation of this compound and the determination of its structure has been described by L. D. Hohenshutz, et al., *Phytochemistry*, 20, 811 (1981). As part of his study of castanospermine, Hohenshutz obtained castanospermine tetra-acetate by the reaction of castanospermine with a very large excess of acetic anhydride but there is no suggestion of any other esters of castanospermine in the article.

DESCRIPTION OF THE INVENTION

The present invention is directed to certain esters and glycoside derivatives of castanospermine. More particularly, it is directed to compounds having the following general formula:

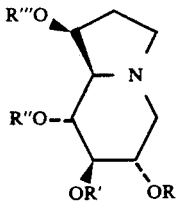

wherein R, R' and R" are independently hydrogen, $C_{1-18}$ alkanoyl, $(R''''-X-)(C_{2-18}$ alkanoyl$)$, $(C_{1-4}$ alkoxy$)-CO-(CH_2)_n-CO-$, $(C_{3-6}$ cycloalkane$)$carbonyl,

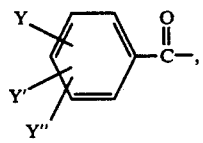

naphthalenecarbonyl optionally substituted by methyl or halogen; phenyl($C_{2-6}$ alkanoyl) or phenyl[$(R''''-X-)C_{2-6}$ alkanoyl]wherein the phenyl is optionally substituted by methyl or halogen; cinnamoyl; pyridinecarbonyl optionally substituted by methyl or halogen; thiophenecarbonyl optionally substituted by methyl or halogen; furancarbonyl optionally substituted by methyl or halogen; or a glycosyl radical, an O-methylglycosyl radical or a glycosyl radical acylated by Ac, each containing from 1 to 3 hexose or pentose units with attachment at the 1-position of the glycosyl radical; R''' is hydrogen, $C_{1-18}$ alkanoyl, $(R''''-X-)(C_{2-18}$ alkanoyl$)$, $(C_{1-4}$ alkoxy$)-CO-(CH_2)_n-CO-$, $(C_{3-6}$ cycloalkane$)$carbonyl,

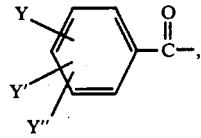

naphthalenecarbonyl optionally substituted by methyl or halogen, phenyl ($C_{2-6}$ alkanoyl) or phenyl-[$(R''''-X-)C_{2-6}$ alkanoyl]wherein the phenyl is optionally substituted by methyl or halogen; cinnamoyl; pyridine-carbonyl optionally substituted by methyl or halogen; thiophenecarbonyl optionally substituted by methyl; furancarbonyl optionally substituted by methyl; n is a whole number from 0 to 4; Y is hydrogen, $C_{1-4}$ alkyl, phenyl, $C_{1-4}$ alkoxy, halogen, trifluoromethyl, $C_{1-4}$ alkylsulfonyl, $C_{1-4}$ alkylmercapto, $(C_{1-4}$ alkoxy$)$carbonyl, cyano or amino, $(C_{1-4}$ alkyl$)$amino or $(C_{1-4}$ alkyl$)_2$ amino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; R'''' is hydrogen or $C_{1-4}$ alkyl; X is O, S or NH; with R, R', R" R''' selected in such a way that at least two of them but not more than three of them are hydrogen; or the pharmaceutically acceptable salts of the aforesaid compounds.

The $C_{1-18}$ alkanoyl groups referred to above can be straight- or branched-chain and can be exemplified by formyl, acetyl, propionyl, butyryl, isobutyryl, hexanoyl, octanoyl, decanoyl and hexadecanoyl. $C_{2-18}$ Alkanoyl is defined similarly except it does not include formyl. Examples of $(R''''-X-)(C_{2-18}$ alkanoyl$)$ groups are 3-hydroxypropanoyl, 3-mercaptopropanoyl, 2-butoxypropanoyl, 2-(methylthio)propanoyl and 2-aminobutanoyl. The group $(C_{1-4}$ alkoxy$)-CO-(CH_2)_n-CO-$ describes an acyl group derived from an alkanedicarboxylic acid containing n+2 carbon atoms and having one of the ackd groups esterified with an alkyl group containing from 1 to 4 carbon atoms. The $C_{3-6}$ cycloalkane groups referred to above can be exemplified by cyclopropane, cyclopentane and cyclohexane. The halogens referred to above can be exemplified by fluorine, chlorine, bromine, or iodine.

The $C_{2-6}$ alkanoyl groups referred to above (Ac) can be exemplified by acetyl, propionyl, butyryl, isobutyryl, and hexanoyl. The $C_{1-4}$ alkyl groups referred to above, whether alone or as part of an alkoxy, an alkylsulfonyl or an alkylmercapto or some other group, can be straight- or branched-chain alkyl groups containing up to 4 carbon atoms. Examples of various such groups are methyl, ethyl, propyl, butyl, methoxy, ethoxy, butoxy, methylsulfonyl, ethylsulfonyl, methylmercapto and ethylmercapto. The phenyl ($C_{2-6}$ alkanoyl) groups referred to above can be exemplified by benzeneacetyl and benzenepropionyl. In the phenyl[$(R''''-X-)C_{2-6}$ alkanoyl] groups referred to above, the phenyl and the $R''''-X-$ groups are both attached directly to the $C_{2-6}$ alkanoyl group. Examples of such groups are α-hydroxybenzene-acetyl, α-mercaptobenzeneacetyl, α-amino-benzenepropanoyl and β-methoxybenzenepropanoyl. The various naphthalenecarbonyl, pyridinecarbonyl, thiophenecarbonyl and furancarbonyl groups referred to above include the various position isomers and these can be exemplified by naphthalene-1-carbonyl, naphthalene-2-carbonyl, nicotinoyl, isonicotinoyl, thiophene-2-carbonyl, thiophene-3-carbonyl, furan-2-carbonyl and furan-3-carbonyl. The naphthalene, pyridine, thiophene and furan groups can be optionally further substituted as indicated above.

Specific examples of the various glycosyl radicals are glucosyl, galactosyl, mannosyl, fucosyl, ribosyl, 2-deoxy-glucosyl, 3-O-methylglucosyl, cellobiosyl, maltobiosyl, maltotriosyl, cellotriosyl, arabinosyl and xylosyl. The term glycosyl acylated by Ac indicates a glycosyl redical in which hydroxy groups are esterified with Ac radicals. Particularly preferred are the compounds wherein R is 1-glucosyl, 1-L-fucosyl or 1-cellobiosyl.

Acid addition salts with pharmaceutically acceptable acids referred to above are equivalent to the amines for the purposes of this invention. Illustrative of such salts are the salts with inorganic acids such as, for example, hydro-chloric, chloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Preferred compounds of the present invention are those wherein R''' is hydrogen. When R''' is hydrogen, then R, R' and R'' are selected in such a way that at least one of them, but not more than two of them, is hydrogen. A further preferred group of compounds are those wherein R''' is hydrogen R, R' and R'' are 1 or 2 alkanoyl or benzoyl groups with the benzoyl substituted by Y, Y' and Y'' as described above.

The esters of the present invention are prepared by the reaction of castanospermine with an appropriate acid chloride or anhydride in an inert solvent. The halide can be a chloride or bromide; the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited excess of the acid derivative (halide or anhydride) is used, which would mean that up to about a threefold excess of the acylating agent is used. Use of a solvent in relatively large amounts serves to dilute the reactants and hold down the amount of higher acylated products that form. The solvent used is preferably one that will dissolve the reactants used without reacting with them. It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the amount of acylation that takes place. Preferably, the reaction is carried out with cooling in an ice-bath for a period of about 16 hours to give the monoesters with the reaction time extended to a longer period, such as 7 days, if diesters are desired. The reaction can actually be carried out at higher temperatures and, in fact, heating can be used as long as the various factors involved are properly controlled. The fact of the matter is, when the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important when the reaction is carried out under conditions which would favor the isolation of monoesters.

The procedures as described above will generally give 6- or 7-monoesters or 6,7- or 6,8-diesters. Other isomers can be obtained by the appropriate use of blocking groups which can be removed readily and selectively. In addition, it of reactions which would give, with greater specificity, some of the compounds that can also be obtained directly. Some examples of blocking groups which are useful in such procedures are 2-(dibromomethyl)benzoyl esters and 2-iodobenzoyl esters. 1,8-Ketals of castanospermine such as 1,8-O-isopropylidenecastanospermine and 1,8-O-cyclohexylidenecastanospermine can also be used. In addition, alkanoyl groups, preferably those containing 2 to 6 carbon atoms, can be used as blocking groups in the preparation of benzoate and substituted benzoate esters as the members of the former group are preferentially removed by acid treatment.

The use of such blocking groups can be illustrated as follows. Thus, castanospermine can be reacted with 2-(dibromomethyl)benzoyl chloride to give the 6,7-diester. This diester is then further reacted with an appropriate acid halide or anhydride, corresponding to the ester group desired in the final product, to give the castanospermine compound which is thus further esterified at the 8-hydroxy group. The two (dibromomethyl)benzoyl protecting groups are then readily removed by first converting the dibromomethyl substituents to formyl groups (using silver perchlorate and 2,4,6-collidine in aqueous acetone) followed by hydrolysis of the resulting formylbenzoic acid ester groups using morpholine and hydroxide ion to give the castanospermine compound having free hydroxy groups at the 6- and 7-positions and monoesterified at the 8-position with the desired ester group. The indicated procedure can be used in a similar way, proceeding through a 6-[2-(dibromomethyl)benzoyl]monoester, to give the 7,8-diester isomer.

The use of 2-(dibromomethyl)benzoate esters in selective esterification procedures such as those referred to above is described by Chattopadhyaya et al., *J.C.S. Chem. Comm.*, 1979, 987. From the above article and other references cited therein, the specific manner in which the 2-(dibromomethyl)benzoyl ester group can be used as a selective protecting group should be clear to one skilled in the art. The indicated ester group is useful as a selective protecting group because of the fact that it can be readily converted to the corresponding 2-formylbenzoyl ester. Such a 2-formyl ester is then hydrolyzed readily under mild conditions by an intramolecular reaction as described in the article referred to above. Obviously, such an ester would be special and would be clearly distinguished from most esters which require much stronger conditions (i.e., heating in the presence of base or acid) to effect hydrolysis and are only hydrolyzed under such stronger conditions. Thus, when a 2-formylbenzoate is present in a molecule with other ester groups and the compound is subjected to the mild hydrolysis conditions described earlier, only the formylbenzoate would be affected. In particular, no other substituted benzoate ester would be affected in a similar manner.

As far as 2-iodobenzoyl esters are concerned, their use as selectively removable blocking groups would be similar to the use of the 2-(dibromomethyl)benzoyl esters discussed above except that a difference procedure would be used to selectively remove the 2-iodobenzoyl esters. Thus, castanospermine would be reacted with 2-iodobenzoyl chloride to give a mono- or di-ester as desired and this would be further reacted with an appropriate acid halide or anhydride corresponding to the ester group desired in the final product. The iodobenzoyl group or groups are then removed by standard chlorination/aqueous bicarbonate oxidation of the iodo to iodosyl to give 2-iodosobenzoic acid (after acidification) and the castanospermine derivative having a free hydroxy group at the positions previously occupied by the iodobenzoyl ester. This procedure for using iodobenzoyl esters as protecting groups is described by Moss et al., *Tetrahedron Letters*, 28, 5005 (1987).

In the case of 1,8-O-isopropylidenecastanospermine or 1,8-cyclohexylidenecastanospermine, the reaction of this material with an acid chloride in a standard esterification procedure favors the formation of the 6-ester almost exclusively. The isopropylidene or cyclohexylidene group is then removed by treatment with an acid such as 4-toluenesulfonic acid. The starting ketal compounds are themselves obtained from castanospermine 6,7-dibenzoate. This dibenzoate is reacted with 2-methoxypropene or 1-methoxycyclohexene and acid to introduce the 1,8-0-isopropylidene or 1,8-O-cyclohexylidene group and the two benzoate ester groups are removed by hydrolysis with base such as sodium hydroxide or by transesterification with sodium or potassium alkoxide as the catalyst.

The use of alkanoyl groups as blocking groups can be illustrated as follows. Castanospermine 6-butyrate is prepared using 1,8-O-isopropylidenecastanospermine by the general procedure described in the preceding paragraph. The 6-butyrate is then reacted with an acid halide such as benzoyl chloride to give a mixture of castanospermine 1-benzoate 6-butyrate and castanospermine 8-benzoate 6-butyrate. The mixture of diesters is then treated with an equivalent of an acid such as hydrogen chloride in methanol whereupon the butyrate ester group is hydrolyzed without affecting the benzoate ester group because butyrate esters are hydrolyzed much more readily under these conditions. The resulting mixture of castanospermine 1-benzoate and 8-benzoate is then separated by standard procedures such as chromatography to give the individual pure isomers.

To prepare those compounds of the present invention wherein R'''' is hydrogen and those compounds wherein X is NH, the appropriate benzyl substituted or benzyloxycarbonyl substituted (i.e., benzyloxy, benzylthio or benzyloxycarbonylamino) alkanoyl chloride is used in a procedure as described above and then the benzyl group or benzyloxycarbonyl group is removed by standard procedures (i.e., catalytic hydrogenation).

To obtain the glycoside derivatives of the present invention, reacted with an appropriate glycosyl halide or an appropriate glycosyl acetimidate, wherein the glycosyl hydroxy groups are protected as the Ac-esters or with benzyl groups, in an inert solvent followed, if necessary, by catalytic hydrogenation to remove any benzyl groups. The inert solvent used can be a halogenated hydrocarbon such as methylene chloride. The glycosyl halide can be a chloride or a bromide; a preferred acetimidate is trichloroacetimidate.

When an esterified castanospermine is used in the glycoside process, this serves to block the esterified hydroxide groups so that reaction must take place at another, free hydroxy group. By the use of appropriate reaction conditions and isolation procedures as described above, it is possible to obtain various castanospermine esters having, at various positions, a free hydroxy group would then be available for reaction in the glycoside process. Once the coupling of the castanospermine ester with the glycosyl derivative has taken place, any ester groups, either on the glycoside or on the castanospermine nucleus, can be removed by hydrolysis with base, for example, a strong base such as sodium methoxide in methanol. Such a hydrolysis is usually carried out before the catalytic debenzylation process referred to above.

The present compounds are useful in the treatment of diabetes. More specifically, they can be used to prevent the development of excessive hyperglycemia which may be observed in certain diabetic conditions when a glucose precursor is ingested. Thus, when carbohydrate is ingested either as glucose or in a form such as maltose, sucrose or starch in food or drink, the serum glucose level rises to elevated concentrations. In healthy subjects, this hyperglycemic state quickly returns to normal, the glucose in the blood being rapidly metabolized and stored and/or utilized by the organism. In diabetes mellitus, however, the glucose tolerance of the patient is lowered and the abnormally high serum glucose levels which develop remain elevated for prolonged periods of time. A similar response to that seen in man can also be observed in other animals, including livestock, poultry, pet animals and laboratory animals. Such a condition can be described as postprandial hyperglycemia. One method for treating such a condition would be by administration of some agents which would prevent the conversion of complex sugars to glucose and thus prevent the development of the excessive glucose levels. In the present invention, it has been found that, where the high levels of glucose are a result of the hydrolysis of complex sugars, administration of the present castanospermine derivatives inhibits the initial formation of glucose in the blood and thus makes it possible to avoid the problems which would be associated with prolonged high levels of serum glucose.

The mechanism whereby this result is achieved is the following although the utility described above should not be limited by the precise details of this mechanism. Enzymes which catalyze the hydrolysis of complex carbohydrates convert non-absorbable carbohydrate into absorbable sugars. The rapid action of these enzymes lead to acute and undesirable elevations in serum glucose in diabetes. The compounds of the present invention are potent inhibitors of these enzymes and, when co-administered with a carbohydrate meal, they prevent harmful hyperglycemic excursions of this type. It is desirable, however, that the inhibition of these hydrolytic enzymes be selective for those present in the intestine and that is true for the present compounds. Otherwise, inhibition of systemic glycohydrolases may lead to difficulty in the utilization of intracellular carbohydrates. The first enzyme described above is intestinal sucrase whereas the second enzyme is intracellular lysosomal α-glucosidase. The compounds of the present invention were tested for activity against these enzymes by the following procedures.

Intestinal Sucrase

Sucrase was isolated from rat intestine as a crude homogenate using the salt extraction procedure of Kolinska [*Biochem. Biophys. Acta*, 284, 235 (1984)]. Incubation mixtures contained 100 μl of enzyme preparation plus test compound and were incubated for 1 hour before the addition of 6.6 μmole sucrose in 100 μl 0.1M sodium maleate, pH 5.9. The mixtures were incubated an additional 30 minutes and then heat inactivated at 80–100° C. for 3 minutes. Denatured protein was removed by centrifugation. Glucose liberated was determined by glucose dehydrogenase reagents (Seragen Diagnostics).

Lysosomal α-Glucosidase

Lysosomal α-glucosidase was isolated and partially purified from rat liver by the method of Dissous [*Anal. Biochem.*, 116, 35 (1981)] through the ammonium sulfate fractionation steps. Enzyme was incubated with test compound for 1 hour at 37° C. prior to the addition of p-nitro-phenyl-α-D-glucoside in a final volume of 0.6 ml of 0.1M sodium acetate, 25 mM potassium chloride, pH 4.2. Mixtures were incubated for an additional 30 minutes at 37° C. and then heat inactivated at 90° C. Denatured protein was removed by centrifugation. One ml of 0.1M sodium carbonate was added to the supernatant fraction and liberated nitrophenol determined by its absorption at 410 nm.

The results observed when the compounds of the present invention were tested as described above can be summarized as follows:

TABLE I

| Castanospermine Derivative | IC$_{50}$ | |
|---|---|---|
| | Intestinal Sucrase (M) | Lysosomal α-Glucosidase (M) |
| 6-Benzoate | $8 \times 10^{-8}$ | $8 \times 10^{-4}$ |
| 6-(4-Fluorobenzoate) | $2 \times 10^{-7}$ | $4 \times 10^{-6}$ |
| 6-(4-Methylbenzoate) | $3 \times 10^{-7}$ | $1 \times 10^{-3}$ |
| 6-(4-Methoxybenzoate) | $2 \times 10^{-6}$ | $1 \times 10^{-3}$ |
| 7-Benzoate | $2 \times 10^{-6}$ | $2 \times 10^{-4}$ |
| 7-(4-Fluorobenzoate) | $4 \times 10^{-7}$ | $6 \times 10^{-6}$ |
| 7-(2,4-Dichlorobenzoate) | $4 \times 10^{-7}$ | $1 \times 10^{-4}$ |
| 6,7-Dibenzoate | $2 \times 10^{-6}$ | $>10^{-3}$ |
| 6,7-bis(4-Fluorobenzoate) | $4 \times 10^{-6}$ | $>10^{-3}$ |
| 6,8-Dibutyrate | $2 \times 10^{-7}$ | $>10^{-3}$ |
| 7-α-D-Glucopyranoside | $4 \times 10^{-8}$ | $4 \times 10^{-5}$ |
| 8-α-D-Glucopyranoside | $3 \times 10^{-8}$ | $4 \times 10^{-5}$ |
| 8-β-D-Glucopyranoside | $4 \times 10^{-7}$ | $>10^{-4}$ |

From the above results, it can be seen that the present compounds have a lower IC$_{50}$ against intestinal sucrase than against lysosomal α-glucosidase.

The compounds of the present invention were further tested in a sucrose load test to determine their ability to inhibit serum glucose elevation. The procedure can be summarized as follows.

ICR Swiss mice, fasted for overnight, were orally dosed with test compound plus sucrose at 2.0 g/kg. At 30 minutes post sucrose, the animals were sacrificed and their serum glucose concentrations were determined.

The amount of test compound needed to significantly inhibit the serum glucose elevation was determined by comparison to the serum glucose concentration of animals dosed only with sucrose. To test duration of action, mice were orally dosed twice. The initial dose was test compound or vehicle. After 1, 2, or 3 hours, the mice were dosed with sucrose at 2.0 g/kg. After an additional 30 minutes post sucrose, the animals were sacrificed and their serum glucose concentrations were determined. Test compound activity was indicated by a significant difference of serum glucose concentration from the corresponding control. The activity observed is summarized as follows in Table II:

TABLE II

| Castanospermine Derivative | Effective Dose (mg/kg) | Duration Of Action |
|---|---|---|
| 6-Benzoate | 1 | 1 hour |
| 6-(4-Fluorobenzoate) | 5 | — |
| 7-Benzoate | 5 | — |
| 7-(4-Fluorobenzoate) | 5 | 2 hours |
| 7-(2,4-Dichlorobenzoate) | 20 | — |
| 6,7-Dibenzoate | 20 | — |

Sprague Dawley rats, fasted overnight, were orally dosed with test compound plus sucrose at 2.0 g/kg. At times of 0, 0.5, 1.0, 1.5, 2.0, 2.5 and 3.0 hours post dose, plasma samples were analyzed for glucose concentration. To test duration of action, rats were orally dosed twice. The initial dose was water or test compound at an effective dose. After 1 or 4 hours, rats were dosed with sucrose at 2.0 g/kg. Plasma samples were taken at 0.5, 1.0, 1.5, 2.0, 2.5 and 3.0 hours and analyzed for glucose concentration. Test compound activity was indicated by a significant difference from the corresponding control using area-under-the curve. The activity observed is summarized as follows in Table III:

TABLE III

| Castanospermine Derivative | Effective Dose (mg/kg) | Duration Of Action |
|---|---|---|
| 7-α-D-Glucopyranoside | 0.3 | $\geq 4$ hours |
| 8-α-D-Glucopyranoside | 3.0 | $\geq 4$ hours |
| 8-β-D-Glucopyranoside | 10.0 | $\geq 4$ hours |

In practicing the method of this invention, an amount of one of the compounds effective to inhibit postprandial hyperglycemia is administered to an animal in need thereof by a suitable route. For the purposes of this invention, oral administration is preferred.

The effective amount of the compound, that is, the amount sufficient to inhibit postprandial hyperglycemia, depends on various factors such as the size, type and age of the animal to be treated, the particular compound or pharmaceutically acceptable salt employed, the frequency of administration, the severity of the condition and the time of administration. Generally speaking, the compounds would be administered orally at a dose of 0.1 mpk to 50 mpk, with a dose of 0.5 mpk to 5 mpk being preferred. More specifically, the present compounds would be administered to humans in single unit doses containing 35 mg to 350 mg of active ingredient with the material being administered three times a day at mealtime.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Penna.

The following examples are presented to illustrate the present invention. However, they should not be construed as limiting it in any way.

EXAMPLE 1

A slurry of 4.0 g of castanospermine in 140 ml of pyridine was stirred at room temperature for 30 minutes until essentially all of the solids had dissolved. The solution was cooled to 0° C. in an ice/water bath, and a solution of 5.85 ml of benzoyl chloride in 15 ml of pyridine was added dropwise over 15 minutes under nitrogen. After the addition, the reaction was stirred at 8° C. overnight.

The reaction mixture was partitioned between 225 ml methylene chloride and 300 ml water. The organic layer was separated and the aqueous layer extracted with two 225-ml portions of methylene chloride. The combined organic layers were washed successively with 150 ml of 0.5N hydrochloric acid, saturated sodium carbonate, water and saturated sodium chloride solutions, and then dried over sodium sulfate. Evaporation of solvents under reduced pressure gave 2.9 g of a tan glassy residue.

This material was slurried in chloroform and a white precipitate formed. These solids were isolated to afford 910 mg of a white powder. Thin layer chromatography (85:15, ethyl acetate:methanol) analysis showed the material to be composed of two components (Rf 0.33 and Rf 0.26). The solid mixture was slurried in 45 ml of 4:1 ethyl acetate:methanol and filtered. The residue was dried in vacuo to provide 350 mg of [1S-(1α, 6β, 7β, 8β, 8αβ) ]-octahydro-1,6,7,8-indolizinetetrol 6-benzoate as a white powdery solid melting at about 233-236° C., with decomposition. This corresponded to the less polar component of the mixture. NMR (DMSO-d$_6$) δ1.5-2.2 (m, 5H), 2.9-3.6 (m, 4H), 4.1 (m, 1H, C$_1$-H), 4.3 (d, 1H, —OH) 4.7 (d, 1H, —OH), 4.8 (sextet, 1H, C$_6$—H), 5.1 (d, 1H, —OH), 7.6-8.1 (m, 5H, aryl). MS (CI-CH$_4$) 294 (MH+), 276 (MH+—H$_2$O), 172 (MH+—PhCO$_2$H).

The filtrate from above was condensed and fractionated by preparative thin layer chromatography (silica gel, 80:20, ethyl acetate:methanol) to provide 120 mg of the more polar component, [1S-(1α, 6β, 7α, 8β, 8αβ) ]-octahydro-1,6,7,8-indolizinetetrol 7-benzoate as a white powdery solid melting at about 200-202° C. NMR (DMSO-d$_6$+D$_2$O) 1.5-2.2, (m, 5H), 2.9-3.1 (m, 2H), 3.6-3.8 (m, 2H), 4.1 (m, 1H, C$_1$—H), 4.8 (t, 1H, C$_7$—H), 7.4-8.1 (m, 5H, aryl). MS (CI—CH$_4$) 294 (MH+), 276 (MH+—$^H$$_2$O), 172 (MH+—$^{PhCO}$$_2$H). This compound has the following structural formula:

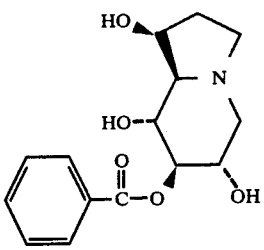

EXAMPLE 2A

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0-4° C. for 7 days. Water, 10 ml, was added and the mixture was evaporated to dryness in vacuo. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf=0.42 and Rf=0.11). The mixture was separated by preparative high pressure liquid chromatography (silica gel, 1:1 ethyl acetate:hexane) to provide 1.9 g (48%) of the more polar [1S-(1α, 6β, 7β, 8β, 8αβ)]-octahydro-1,6,7,8-indolizinetetrol 6,7-dibenzoate as a dry foam melting at about 79-81° C. NMR (DMSO-d$_6$/D$_2$O) δ 1.5-2.3 (m, 5H), 3.0-3.4 (m, 2H), 3.9 (t, 1H), 4.2 (m, 1H, C$_1$—H), 5.15 (m, 1H, C$_6$—H), 5.3 (t, 1H, C$_7$—H), 7.4-8.0 (m, 10H, aryl). MS (FAB—Xe) 398 (MH+), 380 (MH+—H$_2$O), 276 (MH+—PhCO$_2$H). The less polar component (Rf=0.42) was isolated as a dry foam melting at about 75-78° C. which was [1S-(1α, 6β, 7α, 8β, 8αβ)]-octahydro-1,6,7,8-indolizinetetrol 6,7-tibenzoate.

EXAMPLE 2B

Castanospermine (38 g) was added to 250 ml of pyridine and the mixture was cooled at 0° C. while 27.9 g of benzoyl chloride was added dropwise. After this addition was complete, the mixture was stirred at room temperature for 4 hours and then cooled again to 0° C. An additional 27.9 g of benzoyl chloride was added and the mixture was stirred at room temperature for 6 days. After dilution with 20 ml of water, the mixture was evaporated to dryness in vacuo to leave a syrupy golden residue which was stirred vigorously with 100 ml of 3N hydrochloric acid and 400 ml of methylene chloride. The white amorphous solid which formed was [1S-(1α, 6β, 7α, 8β, 8αβ) ]-octahydro-1,6,7,8-indolizinetetrol 6,7-dibenzoate hydrochloride and this was separated by filtration and dried.

EXAMPLE 3

When the procedure of Example 1 was repeated using castanospermine and the appropriate acid chloride, the following compounds were obtained:

[1S-(1α, 6β, 7α, 8β, 8αβ) ]-octahydro-1,6,7,8-indolizinetetrol 6-(4-fluorobenzoate) melting at about 216-218° C.

[1S-(1α, 6β, 7α, 8β, 8αβ) ]-octahydro-1,6,7,8-indolizinetetrol 7-(4-fluorobenzoate) melting at about 190-193° C.

[1S-(1α, 6β, 7α, 8β, 8αβ) ]-octahydro-1,6,7,8-indolizinetetrol 7-(2,4-dichlorobenzoate) melting at about 179-181° C.

[1S-(1α, 6β, 7α, 8β, 8αβ) ]-octahydro-1,6,7,8-indolizinetetrol 6-(4-bromobenzoate) melting at about 234-235° C.

[1S-(1α, 6β, 7α, 8β, 8αβ) ]-octahydro-1,6,7,8-indolizinetetrol 7-(4-bromobenzoate) melting at about 199-202° C.

[S-(1α, 6β, 7α, 8β, 8αβ) ]-octahydro-1,6,7,8-indolizinetetrol 6-(4-methoxybenzoate) melting at about 221-224° C.

EXAMPLE 4

When the procedure of Example 2 was repeated using castanospermine and 4-fluorobenzoyl chloride, the product obtained was [1S-(1α, 6β, 7α, 8α, 8αβ) ]-octahydro-1,6,7,8-indolizinetetrol 6,7-bis(4-fluorobenzoate) melting at about 82-84° C.

EXAMPLE 5

To a suspension of 3 g of castanospermine in 30 ml of pyridine at 0° C. was added dropwise a solution of 3 g of 4-methylbenzoyl chloride. After the addition, the mixture wad allowed to warm to room temperature and then heated at 55° C. for 24 hours. The reaction mixture was diluted with 10 ml of water and evaporated to dryness in vacuo. The resulting residue was stirred in 150 ml of a 1:2 mixture of water: methylene chloride. The insoluble material was separated by filtration to provide an amorphous off-white solid which was dissolved in 60 ml of hot methanol, treated with 0.5 g of activated charcoal and filtered. The colorless filtrate was cooled to give colorless crystals of [1S-(1α, 6β, 7α, 8β, 8αβ) ]-octahydro-1,6,7,8-indolizinetetrol 6-(4-methylbenzoate) melting at about 255-258° C. with decomposition (580 mg, 12% yield).

The two-phase water/methylene chloride mixture obtained above was evaporated to dryness and the residue was dissolved in 50 ml of a 1:2 mixture of methanol:ethyl acetate. The solution was fractionated by preparative high pressure liquid chromatography (silica gel, 9:1 ethyl acetate: methanol) and fractions containing the more polar component (i.e., more polar than the 6-ester obtained in the preceding paragraph) were collected and evaporated in vacuo to provide a colorless solid which was [1S-(1α, 6β, 7α, 8β, 8αβ) ]-octahydro-1,6,7,8-indolizinetetrol 7-(4-methylbenzoate) melting at about 220-223° C. with decomposition (210 mg, 4% yield).

EXAMPLE 6

When the procedure of Example 5 was repeated using castanospermine and the appropriate acid chloride, the following esters were obtained:
6-(2-Methylbenzoate) melting at about 213-215° C.
6-(3-Methylbenzoate) melting at about 212° C. with decomposition.
6-(2-Thiophenecarboxylate) melting at about 214-215° C.
6-(2-Furancarboxylate) melting at about 209-212° C.

In addition, when the procedure of Example 5 is repeated using castanospermine and the appropriate acid chloride, the following esters are obtained:
6-Hexadecanoate.
6-Methoxalate.
6-(3-Ethoxycarbonyl)propionate.
7-(3-Methylbenzoate).
6-(3-Trifluoromethylbenzoate).
6-(4-Methylsulfonylbenzoate).
6-(4-Methylmercaptobenzoate).
6-(3-Cyanobenzoate).
6-(4-Dimethylaminobenzoate).
6-(3,4-Methylenedioxybenzoate).
6-(3,4,5-Trichlorobenzoate).
7-(3,4,5-Trichlorobenzoate).
6-(2,4-Dimethylbenzoate).
6-(2-Carbomethoxybenzoate).
6-(2-Naphthalenecarboxylate).
7-(2-Naphthalenecarboxylate).
6-(4-Methyl-2-naphthalenecarboxylate).
6-(Benzeneacetate).
7-(Benzeneacetate).
6-(4-Chlorobenzeneacetate).
6-(Benzenepropionate).
6-(Cinnamate).
7-(Cinnamate).
6-(Cyclohexanecarboxylate).
6-Nicotinoate.
6-Isonicotinoate.
6-(2-Methyl-4-pyridinecarboxylate).
6-(6-Chloro-3-pyridinecarboxylate).
6-(5-Methyl-2-thiophenecarboxylate).
6-(5-Methyl-2-furancarboxylate).

EXAMPLE 7

Castanospermine (350 mg) was added to 5 ml of pyridine and stirred under nitrogen at room temperature. Butyric anhydride (0.97 g) was added dropwise and the mixture was kept at room temperature for 24 hours. The reaction mixture was evaporated to dryness in vacuo to leave a syrupy residue. The residue was dissolved in ether and a colorless solid precipitated when pentane was added. Recrystallization of the solid from a mixture of ether and petroleum ether gave colorless needles of [1S-(1α, 6β, 7α, 8β, 8αβ) ]-octahydro-1,6,7,8-indolizinetetrol 6,8-dibutanoate melting at about 110-111° C. (22 mg, 4% yield). NMR (CDCl$_3$) δ 3.7 (t, 1H, C$_7$—H), 4.1 (m, 1H, C$_1$—H), 4.85 (t, 1H, C$_8$—H), 5.0 (m, 1H, C$_6$—H. MS (CI—CH$_4$) 330 (MH$^+$) 312 (MH$^+$—H$_2$O).

EXAMPLE 8

When the procedure of Example 7 is repeated using acetic anhydride, propionic anhydride or caproic anhydride in place of the butyric anhydride, the corresponding 6,8-diesters are obtained.

EXAMPLE 9

To a stirred suspension of 1.5 g of castanospermine in 15 ml of pyridine cooled at 0° C. in an ice-bath was added dropwise 1.0 g of butyryl chloride. The mixture was stirred at room temperature for 3 days and added to a 1:1 mixture of water:methylene chloride (400 ml). After partitioning, the aqueous phase was concentrated in vacuo to provide an oily residue which was fractionated by radial thin layer chromatography (silica gel, 2 mm thickness plate, 2:8 methanol: chloroform) to provide 68 mg of [1S-(1α, 6β, 7α, 8β, 8αβ) ]-octahydro-1,6,7,8-indolizinetetrol 6-butanoate, homogeneous by thin layer chromatography (silica gel, 2:8 methanol: chloroform, Rf=0.5). Recrystallization of the product from 5:95 isopropanol:hexane gave a colorless solid melting at 113-114° C. NMR (CDCl$_3$) δ 3.5-3.8 (2t, 2H, C$_7$—H, and C$_8$—H), 4.4 (m, 1H, C$_1$—H), 4.95 (m, 1H, C$_6$—H). MS (CI—CH$_4$) 260 (MH$^+$), 242 (MH$^+$—H$_2$O), 172 (MH$^+$—C$_3$H$_7$CO$_2$H). Similarly, when the above procedure was repeated using acetyl chloride or propionyl chloride, the following monoesters were obtained:

[1S-(1α, 6β, 7α, 8β, 8αβ) ]-octahydro-1,6,7,8-indolizinetetrol 6-acetate melting at about 188–189° C.

[1S-(1α, 6β, 7α, 8β, 8αβ) ]-octahydro-1,6,7,8-indolizinetetrol 7-propionate melting at about 153–155° C.

EXAMPLE 10

To a mixture of 1.0 g of castanospermine and 30 ml of pyridine at 0° C. under a blanket of nitrogen was added 12.2 g of isonicotinoyl chloride hydrochloride. The resulting yellow solution was heated at 55° C. for 41 hours. A 6-mg quantity of 4-dimethylaminopyridine was added and reflux was continued for an additional 24 hours. The reaction solution was concentrated and applied to a 700-ml volume column of Kieselgel 60 and eluted with 80:20:1:: chloroform:methanol: ammonium hydroxide. After collection of a 300-ml forerun, 100-ml fractions were collected. Fractions 11–21 were concentrated to afford 180 mg of material which was applied to a radial chromatography plate (2 mm; Kieselgel 60 PF-254) and eluted with 9:1:: chloroform:methanol. After eluting three bands, fractions containing a fourth band were combined and concentrated to give [1S-(1α, 6β, 7α, 8β, 8αβ) ]-octahydro-1,6,7,8-indolizinetetrol 7-isonicotinoate as a white solid. NMR (DMSO-d₆) δ 8.81 (d, J=5.9 Hz, 2H, pyridyl protons ortho to (N), 7.87 (d, J=5.9 Hz, 2H, pyridyl protons meta to (N), 4.85 (dd, J=9.2 Hz, J=9.2Hz, 1H, C₇—H).

EXAMPLE 11

To a stirred solution of 1.7 g of [1S-(1α, 6β, 7α, 8β, 8αβ) ]-octahydro-1,6,7,8-indolizinetetrol 60 ml of methylene chloride under nitrogen and cooled at −30° C. was added 3.8 g of 2,3,4,6-tetra-O-(phenylmethyl) -α-D-glucopyranosyl) trichloroacetimidate [prepared according to the procedure of R. R. Schmidt and J. Michel, *Angew. Chem. Int. Ed. Engl.* 19, 731–32 (1980)]. This was followed by dropwise addition of 1.4 g of boron trifluoride etherate. The mixture was kept at −10° C. for 72 hours and then washed successively with 60 ml of aqueous sodium bicarbonate solution and 60 ml of brine. The organic extract was concentrated in vacuo to give a thick syrup. Thin layer chromatography analysis (silica gel, 4:6 ethyl acetate:hexane) indicated that a less polar material of Rf 0.31 had formed. The mixture was fractionated on preparative high pressure liquid chromatography (silica gel, 4:6 ethyl acetate:hexane as eluent) to provide 810 mg (21%) of the protected glucoside product (a mixture of the α- and β-isomers) and 670 mg (39%) of recovered starting diester. Recrystallization of the product from ether/methanol gave colorless crystals of 6,7-di-O-benzoyl-8-O-(2,3,4,6-tetra-O-(phenylmethyl) -α-D-glucopyranosyl)-[1S-(1α, 6β, 7α, 8β, 8αβ) ]-octahydro-1,6,7,8-indolizinetetrol melting at about 145–147° C. ¹³C NMR (DMSO-d₆)δ 165.4 and 165.0 (2×PhC=O), 95.9 (C₁'). MS (CI—CH₄) 920 (MH+). Evaporation of the solvent from the mother liquor remaining after the recrystallization gave 6,7-di-O-benzoyl-8-O-(2,3,4,6-tetra-O-(phenylmethyl)-β-D-gluco-pyranosyl)-[1S-(1α, 6β, 7α, 8β, 8αβ) ]-octahydro-1,6,7,8indolizinetetrol. (This β-product was obtained because the condensation produced approximately 20% of the β-D-glucopyranosyl isomer.)

EXAMPLE 12

6,7 - Di - O - benzoyl - 8 - O - (2,3,4,6 - tetra - O - (phenylmethyl)-α-D-glucopyranosyl)-[1S-1α, 6β, 7α. 8β, 8αβ)]-octahydro-1,6,7,8-indolizinetetrol (460 mg) was added to a stirred solution of 20 ml of methanol under nitrogen. After addition of 5 drops of sodium methoxide solution (4.4M in methanol) the mixture was stirred at room temperature for 18 hours. The mixture was evaporated to dryness and the residue was dissolved in 50 ml of ethyl acetate. The solution was washed twice with brine (20 ml) and evaporated in vacuo to leave a syrup. The syrupy residue was taken up in 8 ml of glacial acetic acid containing 100 mg of 10% Pd/C and hydrogenated on a Parr apparatus (3.5 atmospheres of hydrogen) for 72 hours. The catalyst was filtered and 100 mg of fresh 10% Pd/C was added. The mixture was further hydrogenated (1.0 atmosphere of hydrogen) at 70° C. for 6 hours. After filtering to remove the catalyst, the filtrate was evaporated to dryness and the thick residue was redissolved in 15 ml of water. The aqueous solution was washed twice with 50 ml of ether, concentrated in vacuo to about 3 ml and applied to an anion-exchange column (Bio-Rad AG-1-X8, 200–400 mesh, OH⁻ form, 11 cm×2.5 cm-id). The column was eluted with distilled water and 8 ml fractions were collected. Fractions containing the deprotected glucoside were pooled and lyophilized to provide a white powdery solid which was dissolved in methanol and triturated with acetone to give colorless crystals of 8-O-(α-D-glucopyranosyl)-[1S-(1α, 6β, 7α, 8β, 8αβ)]-octahydro-1,6,7,8-indolizinetetrol, melting at about 208–210° C. (147 mg, 83% yield). NMR (D₂O) δ 1.7 (m, 1H), 2.0–2.4 (m, 4H), 3.0–3.2 (m, 2H), 3.4 (t, 1H), 3.5–3.9 (m, 8H), 4.4 (m, 1H, C₁—H), 5.4 (d, 1H, J₁,₂'=3.9 Hz, C₁'—H, anomeric proton). MS (CI—CH₄) 352 (MH+), 334 (MH+—H₂O). This compound has the following structural formula:

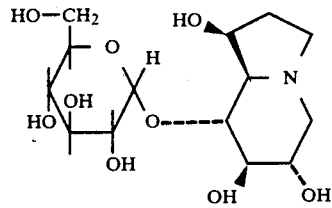

When the above procedure was repeated using 6,7-di-O-benzoyl-8-O-(2,3, 4,6-tetra-O-(phenylmethyl)-β-D-gluco-pyranosyl)-[1S-(1α, 6β, 6α, 8β, 8αβ)]-octahydro-1,6,7,8-indolizinetetrol, the product obtained was 8-O-(β-D-glucò-pyranosyl)-[1S-(1α, 6β, 7α, 8β, 8αβ) ]-octahydro-1,6,7,8-indolizinetetrol (hydrate) melting at about 198–200° C.

EXAMPLE 13

If the procedures of Examples 11 and 12 are repeated starting with [1S-(1α, 6β, 7α, 8β, 8αβ) ]-octahydro-1,6,7,8indolizinetetrol 6,7-dibenzoate and the appropriate glycosyl trichloroacetimidate (obtained as indicated in Example 9), the following products are obtained:

8-O-(β-D-Galactopyranosyl)-[1S-(1α, 6β, 7α, 8β, 8αβ) ]-octahydro-1,6,7,8-indolizinetetrol.

8-O-(α-D-Galactopyranosyl)-[1S-(1α, 6β, 7α, 8β, 8αβ) ]-octahydro-1,6,7,8-indolizinetetrol.

8-O-(6-Deoxy-β-L-galactopyranosyl)-[1S-(1α, 6β, 7α, 8β, 8αβ) ]-octahydro-1,6,7,8-indolizinetetrol.

8-O-(6-Deoxy-α-L-galactopyranosyl)-[1S-(1α, 6β, 7α, 8β, 8αβ) ]-octahydro-1,6,7,8-indolizinetetrol.

8-O-(β-D-Ribofuranosyl)-[1S-(1α, 6β, 7α, 8β, 8αβ) ]-octahydro-1,6,7,8-indolizinetetrol.

8-O-(α-D-Ribofuranosyl)-[1S-(1α, 6β, 7α, 8β, 8αβ) ]-octahydro-1,6,7,8-indolizinetetrol.

8-O-[α-D-Glucopyranosyl-(1→4)-O-β-D-glucopyranosyl ]-[1S-(1α, 6β, 7α, 8β, 8αβ) ]-octahydro-1,6,7,8-indolizinetetrol.

8-O-[α-D-Glucopyranosyl-(1→4)-O-α-D-glucopyranosyl ]-[1S-(1α, 6β, 7α, 8β, 8αβ) ]-octahydro -1,6,7,8-indolizinetetrol.

8-O-[β-D-Glucopyranosyl-(1→4)-O-α-D-glucopyranosyl ]-1S-(1α, 6β, 7α, 8β, 8αβ)-octahydro-1,6,7,8-indolizinetetrol.

8-O-[βD-Glucopyranosyl-(1→4)-O-β-D-glucopyranosyl ]-[1S-(1α, 6β, 7α, 8β, 8αβ)]-octahydro-1,6,7,8-indolizinetetrol.

8-O-(3-0-Methyl-α-D-glucopyranosyl)-[1S-(1α, 6β, 7α, 8β, 8αβ)- ]-octahydro-1,6,7,8-indolizinetetrol. In this case, the [16S-(1α, 6β, 7α, 8β, 8αβ)]-octahydro-1,6,7,8-indolizinetetrol 6,7-dibenzoate was reacted with 3 -0 -methyl-2,4,6-tri-O-(phenylmethyl)-α-D-glucopyranosyl) trichloroacetimidate.

EXAMPLE 14

Castanospermine (0.38 g) was added to a stirred solution of 5 ml of pyridine and cooled in an ice bath. Benzoyl chloride, 0.96 g, was added dropwise to the mixture and the resulting suspension was kept at 0-4° C. for 18 hours. Ice water, 5 ml, was added and the mixture was diluted with 50 ml of ether. The ethereal solution was separated and washed with 1N hydrochloric acid (2×50 ml), saturated aqueous sodium bicarbonate solution (50 ml) and brine (50 ml). The organic phase was dried with anhydrous magnesium sulfate and evaporated to dryness in vacuo. The resulting residue was redissolved in 3 ml of ether and shown to be a mixture of two major components by thin layer chromatography (6:4 ether:hexane, silica gel, Rf=0.35; 0.20). The mixture was separated by preparative thin layer chromatography (silica gel, 6:4 ether:hexane) to provide 0.30 g (30%) of the less polar (Rf=0.35) [1S-(1α, 6β, 7α, 8β, 8αβ) ]-octahydro-1,6,7,8-indolizinetetrol 1,6,8-tribenzoate as a dry, foamy solid melting at about 85-87° C. NMR (CDCl$_3$/D$_2$O) δ 1.7-2.6 (m,5H), 3.0-4.1 (m, 3H), 5.1-5.7 (m, 3H),7.1-8.2 (m, 15H, aryl). MS (CI—NH$_3$) 502 (MH+), 380 (MH+—PhCO$_2$H). The more polar component (Rf=0.20) was isolated as a dry foam melting at about 75-78° C. and was [1S-(1α, 6β, 7α, 8β, 8αβ) ]-octahydro-1,6,7,8-indolizinetetrol 6,7,8-tribenzoate.

EXAMPLE 15

To a stirred solution of 5.2 g of [1S-(1α, 6β, 7α, 8β, 8αβ) ]-octahydro-1,6,7,8-indolizinetetrol 1,6,8-tribenzoate in 150 ml of methylene chloride under nitrogen and cooled at −20° C. there was added 8.5 g of 2,3,4,6-tetra-O-(phenyl-methyl)-α-D-glucopyranosyl trichloroacetimidate. This was followed by dropwise addition of 3.0 ml of boron trifluoride etherate. The mixture was kept at −10° C. for 96 hours. After warming to room temperature, the mixture was washed successively with 200 ml of aqueous sodium bicarbonate solution and 200 ml of brine. The organic phase was dried with magnesium sulfate and evaporated in vacuo to provide a thick syrup. Thin layer chromatography analysis (silica gel, 1:3 ethyl acetate:hexane) showed that a less polar material of Rf=0.44 had formed. The mixture was fractionated on preparative medium pressure liquid chromatography (silica gel, 1:3 ethyl acetate:hexane as eluent) to provide 5.7 g (54%) of 1,6,8-tri-O-benzoyl-7-O-(2,3,4,6-tetra-O-phenylmethyl)-α-D-glucopyranosyl)-[1S-(1α, 6β, 7α, 8β, 8αβ) ]-octahydro-1,6,7,8-indolizinetetrol as a thick colorless syrup. $^{13}$C NMR (CDCl$_3$) δ 166.0, 165.9, 165.5 (3×PhC=0), 99.4 (C$_{1'}$, J $_{13C-1H}$=168 Hz). MS (CI—CH$_4$) 1024 (MH+), 902 (MH+—PhCO$_2$H).

EXAMPLE 16

To a suspension of 5.6 g of 1,6,8-tri-O-benzoyl-7-O-(2,3,4,6-tetra-O-(phenylmethyl)-α-D-glucopyranosyl)-[1 S-(1α, 7α, 8β, 8αβ)]-octahydro-1,6,7,8-indolizinetetrol in 100 ml of methanol was added 30 drops of sodium methoxide solution (4.4M in methanol) and the mixture was stirred at room temperature for 18 hours. To the mixture was added 3 g of potassium hydroxide and 5 ml of water and the resulting solution was heated under reflux for 3 days. The mixture was cooled and evaporated to dryness in vacuo. The residue was dissolved in a mixture of 50 ml of ethyl acetate and 10 ml of water. After separating the phases, the aqueous layer was extracted twice with 30-ml portions of ethyl acetate. The organic extracts were combined and evaporated to provide a yellowish, gummy residue. Recrystallization of the product from ether gave 3.42 g (88%) of colorless, fluffy crystals of 7-O-(2,3,4,6-tetra-O-(phenylmethyl)-α-D-gluco-pyranosyl)-[1S-(1α, 6β, 7α, 8β, 8αβ) ]-octahydro-1,6,7,8-indolizinetetrol melting at about 119-120° C. $^1$H NMR (CDCl$_3$) δ 1.5-2.5 (m, 5H), 2.8-4.0 (m, 12H), 4.1-5.0 (m, 12H), 7.0-7.4 (m, 20H, aryl).

EXAMPLE 17

The product from Example 16 (250 mg) was dissolved in 4 ml of glacial acetic acid and 50 mg of 10% Pd/C was added. The mixture was hydrogenated (at 1.0 atmosphere of hydrogen) at 55° C. for 4 hours. After removal of the charcoal catalyst, the acetic acid solution was evaporated to dryness in vacuo. The resulting residue was redissolved in 10 ml of (1:1) methanol-water and stirred for 1 hour with 2.0 g of anion-exchange resin [Bio-Rad AG1-X8 (200-400 mesh, OH−form) ]. The aqueous solution was evaporated to dryness to provide a white powdery solid which was dissolved in methanol and triturated with acetone to give 92 mg of colorless crystals of 7-O-(α-D-glucopyranosyl)-[1S-(1α, 6β, 7α, 8β, 8αβ) ]-octahydro-1,6,7,8-indolizinetetrol, melting at about 203-205° C. (with decomposition). MS (CI—CH$_4$) 352 (MH+), 334 (MH+—H$_2$O).

EXAMPLE 18

A mixture of 5.0 g of [1S-(1α, 6β, 7α, 8β, 8αβ) ]-octahydro1,6,7,8-indolizinetetrol 6,7-dibenzoate hydrochloride, 100 ml of 1,2-dimethoxyethane, 22 ml of 2-methoxypropene and 0.22 g of 4-toluenesulfonic acid monohydrate was refluxed with stirring for 1.5 hours to give a clear solution. The reaction was cooled to 25° C. and diluted with 30 ml of saturated aqueous sodium bicarbonate solution and 60 ml of water. This solution was then extracted twice with methylene chloride and the combined organic extracts were dried over magnesium sulfate and the solvent was evaporated in vacuo to give a light green foam. This material was recrystallized from pentane to give [1S-(1α, 6β, 7α, 8β, 8αβ) ]-1,8-O-isopropylideneoctahydro-1,6,7,8-indolizinetetrol 6,7-dibenzoate as white crystals melting at about 132-133° C. (78.6% yield).

To a solution of 0.34 g of [1S-(1α, 6β, 7α, 8β, 8αβ)]-1,8-O-isopropylideneoctahydro-1,6,7,8-indolizinetetrol 6,7-dibenzoate in 50 ml of tetrahydrofuran, at 25° C., there was added 3.1 ml of 1N aqueous sodium hydroxide in one portion. The reaction mixture was stirred for 24 hours, diluted with 10 ml of saturated brine, and extracted with four portions of methylene chloride. The combined organic extracts were dried with magnesium sulfate and the solvent was evaporated in vacuo to give [1S-(1α, 6β, 7α, 8β, 8αβ)]-1,8-O-isopropylideneoctahydro-1,6,7,8-indolizinetetrol as a clear glass which was used without further purification (95% yield). 1H NMR (CDCl3, 300 MHz) δ 4.5 (d, 1H), 3.8 (m, 1H), 3.65 (t, 1H), 3.5 (dd, 1H), 1.9 (m, 1H).

EXAMPLE 19

A mixture of 0.3 g of [1S-(1α, 6β, 7α, 8β, 8αβ)]-1,8-O-isopropylideneoctahydro-1,6,7,8-indolizinetetrol, 6.0 ml of methylene chloride and 0.54 ml of triethylamine was cooled to 0° C and 0.18 ml of benzoyl chloride was added dropwise with stirring. The reaction was then stirred at 0-5° C. for 24 hours before dilution with 10 ml of water and 3 ml of saturated aqueous sodium bicarbonate solution. The layers were separated and the aqueous layer was extracted twice with methylene chloride. The combined organic layers were then dried over magnesium sulfate and the solvent was evaporated in vacuo to give a crude solid product. This solid was recrystallized from ethyl acetate/pentane (1:2) to give [1S-(1α, 6β, 7α, 8β, 8αβ)]-1,8-O-isopropylideneoctahydro-1,6,7,8-indolizinetetrol 6-benzoate as white needles melting at about 181-183° C. (77.9% yield).

A solution was prepared from 0.2 g of [1S-(1α, 6β, 7α, 8β, 8αβ)]-1,8-O-isopropylideneoctahydro-1,6,7,8-indolizinetetrol 6-benzoate and 10 ml of methanol. To this solution, at 25° C., was added 0.34 g of 4-toluenesulfonic acid monohydrate in one portion. The reaction was stirred for one hour and the mixture was then diluted with 30 ml of methylene chloride, 10 ml of saturated aqueous sodium bicarbonate solution, and 10 ml of saturated brine. The layers were separated, the aqueous layer was extracted five times with methylene chloride, and the combined organic layers were dried over magnesium sulfate. The solvent was then evaporated in vacuo to give [1S-(1α, 6β, 7α, 8β, 8αβ)]-octahydro-1,6,7,8-indolizinetetrol 6-benzoate as a white powder melting at about 233-235° C. with decomposition (91% yield).

EXAMPLE 20

A suspension of 4 g of [1S-(1α, 6β, 7α, 8β, 8αβ)]-1,8-O-iso-propylideneoctahydro-1,6,7,8-indolizinetetrol 6,7-dibenzoate hydrochloride in 100 ml of chloroform was stirred vigorously with 150 ml of saturated aqueous sodium bicarbonate for 30 minutes. The organic layer was separated and dried over magnesium sulfate and the solvent was evaporated in vacuo to give a syrup which crystallized to give solid [1S-(1α, 6β, 7α, 8β, 8αβ)]-1,8-O-isopropylideneoctahydro-1,6,7,8-indolizinetetrol 6,7-dibenzoate upon the addition of 40 ml of methanol. The resultant slurry was then stirred and two drops of 25% sodium methoxide in methanol was added; stirring was continued at room temperature for 3 days. The solvent was then evaporated from the mixture in vacuo and the residual solid was redissolved in 100 ml of chloroform. Three equivalents of triethylamine was added followed by the dropwise addition of 1-2 equivalents of 2-furancarbonyl chloride and the resulting mixture was stirred at room temperature for 24 hours.

The crude reaction mixture obtained above was diluted with 20 ml of water and 6 ml of saturated aqueous sodium bicarbonate solution. The layers were mixed thoroughly and then separated. The aqueous phase was extracted twice with methylene chloride and the combined organic layers were dried over magnesium sulfate. The solvent was then evaporated to leave a brown syrup. This syrupy residue was applied to a silica gel column and eluted with ethyl acetate. The fractions containing the desired product were combined and the solvent was evaporated in vacuo to provide a yellowish syrup which crystallized on standing. A portion of this product was dissolved in 10 ml of methanol at room temperature and 0.20 g of 4-toluenesulfonic acid hydrate was added. The resultant solution was first stirred under nitrogen at room temperature for two hours and then heated at reflux for two hours. The resulting mixture was dissolved in methanol/ethyl acetate (1:4) and applied to a silica gel column and the column was eluted with methanol/ethyl acetate (1:9). The fractions containing the desired product were combined and the solvent was evaporated to leave a residue which crystallized on standing to give slightly off-white plates of [1S-(1α, 6β, 7α, 8β, 8αβ)]-octahydro-1,6,7,8-indolizinetetrol 6-(2-furancarboxylate) melting at about 209-212° C.

What is claimed is:

1. A compound of the formula:

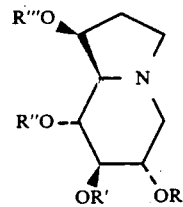

wherein R, R' and R'' are independently hydrogen, $C_{1-18}$ alkanoyl, (R''''—X—) ($C_{2-18}$ alkanoyl), ($C_{1-4}$ alkoxy)—CO—$(CH_2)_n$—

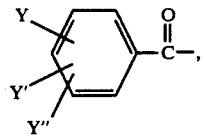

CO—, ($C_{3-6}$ cycloalkane)carbonyl, naphthalenecarbonyl optionally substituted by methyl or halogen; phenyl($C_{2-6}$ alkanoyl) or phenyl[(R''''—X—)$C_{2-6}$ alkanoyl] wherein the phenyl is optionally substituted by methyl or halogen; cinnamoyl; pyridinecarbonyl optionally substituted by methyl or halogen; thiophenecarbonyl optionally substituted by methyl or halogen; furancarbonyl optionally substituted by methyl or halogen; or a glycosyl radical, an O-methylglycosyl radical or a glycosyl radical acylated by Ac, each containing from 1 to 3 hexose or pentose units with attachment at the 1-position of the glycosyl radical; R''' is hydrogen, $C_{1-18}$ alkanoyl, R''''—X—)-$C_{2-18}$ alkanoyl), ($C_{1-4}$ alkoxy)—CO—$(CH_2)_n$—CO—, ($C_{3-6}$ cycloalkane)carbonyl,

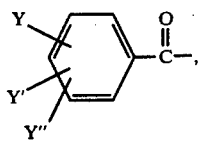

naphthalenecarbonyl optionally substituted by methyl or halogen, phenyl ($C_{2-6}$ alkanoyl) or phenyl[(R''''—X—)$C_{2-6}$ alkanoyl]wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; n is a whole number from 0 to 4; Y is hydrogen, $C_{1-4}$ alkyl, phenyl, $C_{1-4}$ alkoxy, halogen, trifluoromethyl, $C_{1-4}$ alkylsulfonyl, $C_{1-4}$ alkylmercapto, ($C_{1-4}$ alkoxy)carbonyl, cyano, amino, ($C_{1-4}$ alkyl)amino or ($C_{1-4}$ alkyl)$_2$ amino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; Ac is benzoyl or $C_{2-6}$ alkanoyl; R'''' is hydrogen or $C_{1-4}$ alkyl; X is O, S or NH; with R, R', R'' and R'''' selected in such a way that at least two of them but not more than three of them are hydrogen; or the pharmaceutically acceptable salts of the aforesaid compounds.

2. A compound according to claim 1 having the formula:

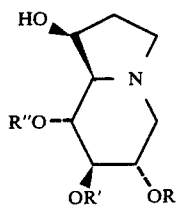

wherein R, R' and R'' are independently hydrogen, $C_{1-18}$ alkanoyl, ($C_{1-4}$ alkoxy)—CO—(CH$_2$)$_n$—CO—, cyclohexanecarbonyl,

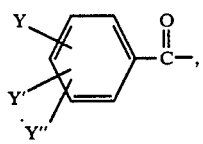

naphthalenecarbonyl optionally substituted by methyl or halogen; phenyl ($C_{2-6}$ alkanoyl) wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; or a glycosyl radical, an O-methylglycosyl radical or a glycosyl radical acylated by Ac, each containing from 1 to 3 hexose or pentose units with attachment at the 1-position of the glycosyl radical; n is a whole number from 0 to 4: Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, ($C_{1-4}$ alkoxy) carbonyl, cyano or dimethylamino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; Ac is benzoyl or $C_{2-6}$ alkanoyl; with R, R' and R'' being selected in such a way that at least one of them, but not more than two of them, is hydrogen; or the pharmaceutically acceptable salts of the aforesaid compounds.

3. A compound according to claim 1 having the formula:

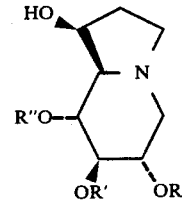

wherein R, R' and R'' are independently hydrogen, $C_{1-18}$ alkanoyl, ($C_{1-4}$ alkoxy)—CO—(CH$_2$)$_n$—CO—, cyclohexanecarbonyl,

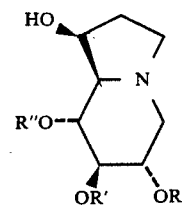

naphthalenecarbonyl optionally substituted by methyl or halogen; phenyl ($C_{2-6}$ alkanoyl) wherein the phenyl is optionally substituted by methyl or halogen; cinnamoyl; pyridinecarbonyl optionally substituted by methyl; furancarbonyl optionally substituted by methyl; n is a whole number from 0 to 4; Y is hydrogen, $C_{1-4}$ alkyl, $C_{1-4}$ alkoxy, halogen, trifluoromethyl, $C_{1-4}$ alkyl-sulfonyl, $C_{1-4}$ alkylmercapto, ($C_{1-4}$ alkoxy)carbonyl, cyano or dimethylamino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R, R' and R'' being selected in such a way that at least one of them, but not more than two of them is hydrogen; or the pharmaceutically acceptable salts of the aforesaid compounds.

4. A compound according to claim 1 having the formula:

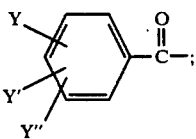

wherein R, R' and R'' are independently hydrogen, $C_{1-18}$ alkanoyl, or

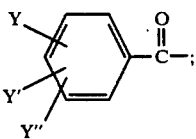

Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, ($C_{1-4}$ alkoxy)carbonyl, cyano or dimethylamino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R, R' and R'' being selected in such a way that at least one of them, but not more than two of them, is hydrogen; or the pharmaceutically acceptable salts of the aforesaid compounds.

5. A compound according to claim 1 having the formula:

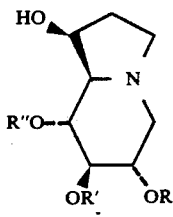

wherein R, R' and R'' are independently hydrogen or

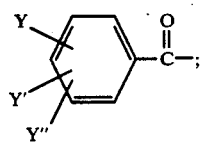

Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ *alkyl*, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R, R' and R'' being selected in such a way that at least one of them, but not more than two of them, is hydrogen; or the pharmaceutically acceptable salts of the aforesaid compounds.

6. A compound according to claim 1 having the formula:

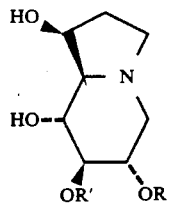

wherein R and R' are independently hydrogen or

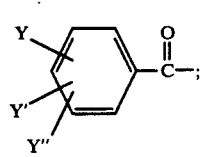

Y is hydrogen, $C_{1-14}$ alkyl, $C_{1-4}$ halogen, trifluoromethyl, $C_{1-4}$ alkylsulfonyl, $C_{1-4}$ alkylmercapto, cyano or dimethylamine; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R and R' being selected in such a way that at least one of them is other than hydrogen; or the pharmaceutically acceptable salts of the aforesaid compounds.

7. A compound according to claim 1 having the formula:

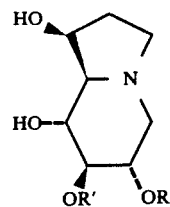

wherein R and R' are independently hydrogen or

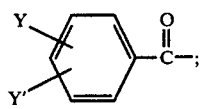

Y is hydrogen, $C_{1-4}$ alkyl, $C_{1-4}$ *alkoxy, halogen, trifluoromethyl*, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; with R and R' being selected in such a way that at least one of them is other than hydrogen; or the pharmaceutically acceptable salts of the aforesaid compounds.

8. A compound according to claim 1 having the formula:

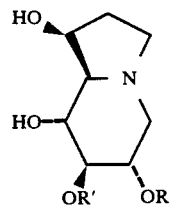

wherein R and R' are independently hydrogen, or

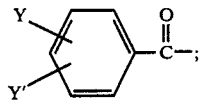

Y is hydrogen or halogen; Y' is hydrogen or halogen; with R and R' being selected in such a way that at least one of them is other than hydrogen; or the pharmaceutically acceptable salts of the aforesaid compounds.

9. A compound according to claim 1 which is [1S(1α, 6β, 7β, 8α, 8αβ) ]-octahydro-1,6,7,8-indolizinetetrol 6benzoate.

10. A compound according to claim 1 which is [1S-(1α, 6β, 7α, 8β, 8αβ) ]-octahydro-1,6,7,8-indolizinetetrol 7benzoate.

11. A compound according to claim 1 which is [1S-(1α, 6β, 7α, 8β, 8αβ) ]-octahydro-1,6,7,8-indolizinetetrol 6-(4-fluorobenzoate).

12. A compound according to claim 1 which is [1S-(1α, 6β, 7α, 8β, 8αβ) ]-octahydro-1,6,7,8-indolizinetetrol 7-(4-fluorobenzoate).

13. A compound according to claim 1 which is [1S-(1α, 6β, 7α, 8β, 8αβ) ]-octahydro-1,6,7,8-indolizinetetrol 6,8-dibutanoate.

14. A compound according to claim 1 having the formula:

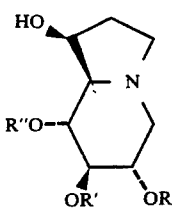

wherein R, R' and R" are independently hydrogen, or a glycosyl radical, an O-methylglycosyl radical or a glycosyl radical acylated by Ac, each containing from 1 to 3 hexose or pentose units with attachment at the 1-position of the 7 glycosyl radical; Ac is benzoyl or $C_{2-6}$ alkanoyl; with R, R' and R" being selected in such a way that at least one of them, but not more than two of them, is hydrogen; or the pharmaceutically acceptable salts of the aforesaid compounds.

15. A compound according to claim 1 which is 8-O-(α-D-glucopyranosyl)-[1S-(1α, 6β, 7α, 8β, 8aβ)]-octahydro-1,6,7,8-indolizinetetrol.

16. A compound according to claim 1 which is [1S-(1α, 6β, 7α, 8β, 8aβ)]octahydro-1,6,7,8indolizinetetrol 6-butanoate.

17. A method for treating diabetes in animals which comprises administering an effective amount of a compound of the formula:

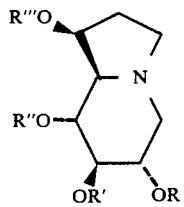

wherein R, R' and R" are independently hydrogen, $C_{1-18}$ alkanoyl, (R""—X—)($C_{2-18}$ alkanoyl), ($C_{1-4}$ alkoxy)—CO—$(CH_2)_n$—CO—, ($C_{3-6}$ cycloalkane)carbonyl,

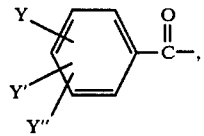

naphthalenecarbonyl optionally substituted by methyl or halogen; phenyl($C_{2-6}$ alkanoyl) or phenyl[(R'''—X—) $C_{2-6}$ alkanoyl] wherein the phenyl is optionally substituted by methyl or halogen; cinnamoyl; pyridinecarbonyl optionally substituted by methyl or halogen; thiophenecarbonyl optionally substituted by methyl or halogen; furancarbonyl optionally substituted by methyl or halogen; or a glycosyl radical, an O-methylglycosyl radical or a glycosyl radical acylated by Ac, each containing from 1 to 3 hexose or pentose units with attachment at the 1-position of the glycosyl radical; R''' is hydrogen, $C_{1-18}$ alkanoyl, (R""—X—)—($C_{2-18}$ alkanoyl), ($C_{1-4}$ alkoxy)—CO—$(CH_2)_n$—CO—, ($C_{3-6}$ cycloalkane)carbonyl,

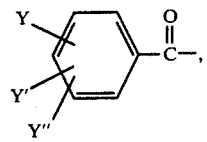

naphthalenecarbonyl optionally substituted by methyl or halogen, phenyl ($C_{2-6}$ alkanoyl) or phenyl [(R""—X—)$C_{2-6}$ alkanoyl] wherein the phenyl is optionally substituted by methyl or halogen; cinnamoyl; pyridinecarbonyl optionally substituted by methyl or halogen; thiophenecarbonyl optionally substituted by methyl or halogen; thiophenecarbonyl optionally substituted by methyl; furancarbonyl optionally substituted by methyl; n is a whole number from 0 to 4; Y is hydrogen, $C_{1-4}$ alkyl, phenyl, $C_{1-4}$ alkoxy, halogen, trifluoromethyl, $C_{1-4}$ alkylsulfonyl, $C_{1-4}$ alkylmercapto, ($C_{1-4}$ alkoxy)carbonyl, cyano, amino, ($C_{1-4}$ alkyl)amino or ($C_{1-4}$ alkyl)$_2$ amino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; R"" is hydrogen or $C_{1-4}$ alkyl; X is O, S or NH; with R, R', R" and R''' selected in such a way that at least two of them but not more than three of them are hydrogen; or the pharmaceutically acceptable salts of the aforesaid compounds.

18. A method according to claim 17 for treating diabetes in animals which comprises administering an effective amount of a compound of the formula:

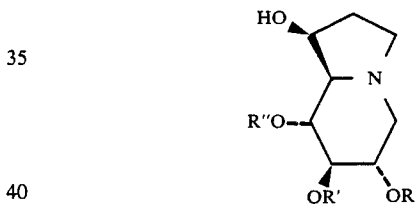

wherein R, R' and R" are independently hydrogen, $C_{1-18}$ alkanoyl, cyclohexanecarbonyl,

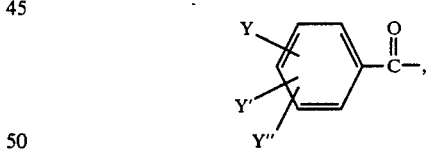

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; or a glycosyl radical, an O-methylglycosyl radical or a glycosyl radical acylated by Ac, each containing from 1 to 3 hexose or pentose units with attachment at the 1-position of the glycosyl radical; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; with R, R' and R" being selected in such a way that at least one of them, but not more than two of them, is hydrogen; or the pharmaceutically acceptable salts of the aforesaid compounds.

19. A method according to claim 17 for treating diabetes in animals which comprises administering an effective amount of a compound of the formula:

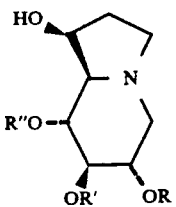

wherein R, R' and R" are independently hydrogen, $C_{1-18}$ alkanoyl, cyclohexanecarbonyl,

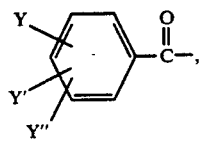

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, R' being selected in such a way that at least one of them, not not more than two of them, is hydrogen; or the pharmaceutically acceptable salts of the aforesaid compounds.

20. A method for treating postprandial hyperglycemia in diabetic individuals which comprises administering an effective amount of a compound of the formula:

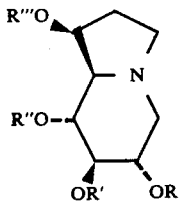

wherein R, R' and R" are independently hydrogen, $C_{1-18}$ alkanoyl, (R''''—X—)($C_{2-18}$ alkanoyl), ($C_{1-4}$ alkoxy)—CO—$(CH_2)_n$—CO—, ($C_{3-6}$ cycloalkane)carbonyl,

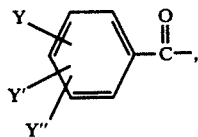

naphthalenecarbonyl optionally substituted by methyl or halogen; phenyl($C_{2-6}$ alkanoyl) or phenyl[(R''''—X—)$C_{2-6}$ alkanoyl]wherein the phenyl is optionally substituted by methyl or halogen; cinnamoyl; pyridinecarbonyl optionally substituted by methyl or halogen; thiophenecarbonyl optionally substituted by methyl or halogen; furancarbonyl optionally substituted by methyl or halogen; or a glycosyl radical, an O-methylglycosyl radical or a glycosyl radical acylated by Ac, each containing from 1 to 3 hexose or pentose units with attachment at the 1-position of the glycosyl radical; R''' is hydrogen, $C_{1-18}$ alkanoyl, (R''''—X—) ($C_{2-18}$ alkanoyl), ($C_{1-4}$ alkoxy)—CO—$(CH_2)_n$—CO—, ($C_{3-6}$ cycloalkane)-carbonyl,

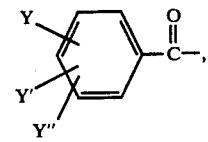

naphthalenecarbonyl optionally substituted by methyl or halogen, phenyl ($C_{2-6}$ alkanoyl) or phenyl[(R''''—X—)$C_{2-6}$ alkanoyl] wherein the phenyl is optionally substituted by methyl or halogen; cinnamoyl; pyridinecarbonyl optionally substituted by methyl or halogen; thiophenecarbonyl optionally substituted by methyl or halogen; furanphenecarbonyl optionally substituted by methyl; furancarbonyl optionally substituted by methyl; n is a whole number from 0 to 4; Y is hydrogen, $C_{1-4}$ alkyl, phenyl, $C_{1-4}$ alkoxy, halogen, trifluoromethyl, $C_{1-4}$ alkylsulfonyl, $C_{1-4}$ alkylmercapto, ($C_{1-4}$ alkoxy)carbonyl, cyano, amino, ($C_{1-4}$ alkyl)amino or ($C_{1-4}$ alkyl)$_2$ amino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; R'''' is hydrogen or $C_{1-4}$ alkyl; X is O, S or NH; with R, R', R" and R''' selected in such a way that at least two of them but not more than three of them are hydrogen; or the pharmaceutically acceptable salts of the aforesaid compounds.

21. A method according to claim 20 for treating postprandial hyperglycemia in diabetic individuals which comprises administering an effective amount of a compound of the formula:

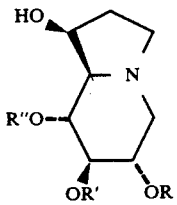

wherein R, R' and R" are independently hydrogen, $C_{1-18}$ alkanoyl, cyclohexanecarbonyl,

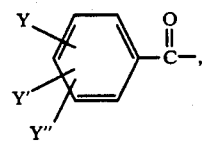

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; or a glycosyl radical, an O-methylglycosyl radical or a glycosyl radical acylated by Ac, each containing from 1 to 3 hexose or pentose units with attachment at the 1-position of the glycosyl radical; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; with R, R' and R" being selected in such a way that at least one of them, but not more than two of them, is hydrogen; or the pharmaceutically acceptable salts of the aforesaid compounds.

22. A method according to claim 19 for treating postprandial hyperglycemia in diabetic individuals which comprises administering an effective amount of a compound of the formula:

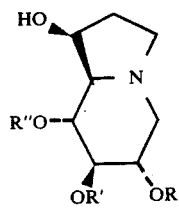

wherein R, R' and R" are independently hydrogen, $C_{1-18}$ alkanoyl, cyclohexanecarbonyl,

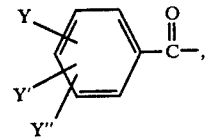

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; thiophenecarbonyl optionally substituted by methyl; furancarbonyl optionally substituted by methyl; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, R' and R" being selected in such a way that at least one of them, but not more than two of them, is hydrogen; or the pharmaceutically acceptable salts of the aforesaid compounds.

* * * * *

UNITED STATES PATENT AND TRADEMARK OFFICE
CERTIFICATE OF CORRECTION

PATENT NO. : 5,017,563

DATED : May 21, 1991

INVENTOR(S) : Paul S. Liu, Barry L. Rhinehart and John K. Daniel

It is certified that error appears in the above-identified patent and that said Letters Patent is hereby corrected as shown below:

At Column 2, line 49, the patent reads "ackd" and should read -- acid --.
At Column 3, line 25, delete "chloric,".
At Column 4, line 22, after "addition, it" insert -- would also be possible to use the blocking groups in a series --.
At Column 9, line 48, the patent reads "6β, 7β, 8β," and should read -- 6β, 7α, 8β, --.
At Column 10, line 30, the patent reads "6β, 7β, 8β," and should read -- 6β, 7α, 8β, --.
At Column 10, line 40, the patent reads "tibenzoate" and should read -- tribenzoate --.
At Column 11, line 10, the patent reads "[S-(" and should read -- [1S-( --.
At Column 12, line 26, after "furancarboxylate)." start a new paragraph.
At Column 13, line 29, the patent reads "(N)" and should read -- N) --.
At Column 13, line 31, the patent reads "(N)" and should read -- N) --.
At Column 13, line 36, after "- indolizinetetrol", insert -- 6,7-dibenzoate in --.
At Column 13, line 65, the patent reads "8indolizinetetrol" and should read -- 8-indolizinetetrol --.
At Column 14, line 51, the patent reads "(1α,6β,6α," and should read -- (1α,6β,7α, --.
At Column 14, line 60, the patent reads "8indolizinetetrol" and should read -- 8-indolizinetetrol --.
At Column 15, line 16, the patent reads "[βD-" and should read -- [β-D- --.
At Column 15, line 21, the patent reads "[16S-(" and should read -- [1S-( --.
At Column 16, line 14, the patent reads "1α,7α,8β," and should read -- (1α,6β,7α,8β, --.
At Column 16, line 54, the patent reads "octahydrol," and should read -- octahydro-1, --.
At Column 17, line 14, after "3.5 (dd, 1H)," insert -- 3.25 (dd, 1H), 3.0 (m, 2H), 2.8 (m, 2H), 2.2 (m, 1H), --.

At Column 21, line 58, the patent reads "$C_{114}$ alkyl" and should read -- $C_{1-4}$ alkyl --.

UNITED STATES PATENT AND TRADEMARK OFFICE
CERTIFICATE OF CORRECTION

PATENT NO.   : 5,017,563

DATED        : May 21, 1991

INVENTOR(S)  : Paul S. Liu, Barry L. Rhinehart and John K. Daniel

Page 2 of 2

It is certified that error appears in the above-identified patent and that said Letters Patent is hereby corrected as shown below:

At Column 21, line 59, the patent reads "dimethylamine" and should read -- dimethylamino --.

At Column 22, line 52, the patent reads "(1α,6β,7β,8α,8αβ)]" and should read -- (1α,6β,7α,8β,8αβ)] --.

At Column 22, line 53, the patent reads "6benzoate." and should read -- 6-benzoate. --.

At Column 22, line 56, the patent reads "7benzoate" and should read -- 7-benzoate --.

At Column 23, line 16, delete "7".

At Column 23, line 26, the patent reads "8indolizinetetrol" and should read -- 8-indolizinetetrol --.

At Column 25, line 37, the patent reads "with R, R' being" and should read -- with R, R' and R" being --.

Signed and Sealed this

Twenty-third Day of March, 1993

Attest:

STEPHEN G. KUNIN

*Attesting Officer*      Acting Commissioner of Patents and Trademarks